(12) United States Patent
Theilacker-Beck et al.

(10) Patent No.: US 8,224,166 B2
(45) Date of Patent: Jul. 17, 2012

(54) LIQUID WARMING BAG AND BAG WARMER

(75) Inventors: Wolfgang Theilacker-Beck, Stuttgart (DE); Matthias Theilacker, Stuttgart (DE); Klaus Schmider, Stuttgart (DE)

(73) Assignee: WWT Technischer Geraetebau GmbH, Stuttgart (DE)

( * ) Notice: Subject to any disclaimer, the term of this patent is extended or adjusted under 35 U.S.C. 154(b) by 454 days.

(21) Appl. No.: 12/458,803

(22) Filed: Jul. 23, 2009

(65) Prior Publication Data

US 2010/0021148 A1    Jan. 28, 2010

(30) Foreign Application Priority Data

Jul. 25, 2008  (EP) .................................... 08013404

(51) Int. Cl.
*A61F 7/08* (2006.01)
(52) U.S. Cl. .................. 392/443; 392/465; 604/113
(58) Field of Classification Search .............. 392/470; 604/113
See application file for complete search history.

(56) References Cited

U.S. PATENT DOCUMENTS

| | | | | |
|---|---|---|---|---|
| 3,295,297 | A | * | 1/1967 | Collins ........................ 96/155 |
| 4,102,655 | A | * | 7/1978 | Jeffery et al. ................. 96/204 |
| 4,680,445 | A | * | 7/1987 | Ogawa ......................... 392/470 |
| 4,681,606 | A | * | 7/1987 | Swan et al. ................... 96/197 |
| 4,847,470 | A | * | 7/1989 | Bakke .......................... 392/470 |
| 5,306,269 | A | * | 4/1994 | Lewis et al. ................. 604/403 |
| 5,733,263 | A | | 3/1998 | Wheatman |
| 6,508,859 | B1 | * | 1/2003 | Zia et al. ......................... 95/46 |
| 7,004,196 | B2 | * | 2/2006 | Schubmehl et al. .......... 137/574 |
| 2006/0000829 | A1 | | 1/2006 | Furnrohr |
| 2011/0046551 | A1 | * | 2/2011 | Augustine et al. ............ 604/113 |
| 2011/0270180 | A1 | * | 11/2011 | Arnold et al. ................ 604/113 |

FOREIGN PATENT DOCUMENTS

| | | |
|---|---|---|
| EP | 0 350 675 | 1/1990 |
| WO | WO 00/12155 | 3/2000 |
| WO | WO 2005/072666 | 8/2005 |

* cited by examiner

*Primary Examiner* — Thor Campbell
(74) *Attorney, Agent, or Firm* — Paul Vincent

(57) ABSTRACT

A liquid heating bag 50 is proposed, in particular, a blood heating bag, with a flow volume 1 that is formed from at least two flexible plastic foils connected to each other by welding at four delimiting edges 3,4,5,6, has a flat, substantially trapezoidal basic shape that is limited by the delimiting edges 3,4,5,6, and an inlet line opening 10 and an outlet line opening 11 for a liquid to be heated that are disposed at an upper delimiting edge 3 of the delimiting edges 3,4,5,6 to be disposed at the top during liquid heating, wherein the upper delimiting edge 3 extends sufficiently obliquely with respect to its adjacent delimiting edges 4,6 that a gas reception volume 8 is formed in the region of an acute angle of the flow volume 1 subtended between the upper delimiting edge 3 and a delimiting edge 6 adjacent thereto, and a liquid flow guiding seam 13 that is formed by connecting the plastic foils in the region of the flow volume 1 and divides the upper delimiting edge 3 into a lower inlet line opening region and an upper outlet line opening region on the gas reception volume side. A degassing opening 23 is disposed at the upper delimiting edge 3 in the region of the gas reception volume 8 between the outlet line opening 11 and the delimiting edge 6 adjacent to the outlet line opening region.

13 Claims, 3 Drawing Sheets

LIQUID WARMING BAG AND BAG WARMER

This application claims Paris Convention priority of EP 08 013-404.2 filed Jul. 25, 2008 the complete disclosure of which is hereby incorporated by reference.

BACKGROUND OF THE INVENTION

The invention relates to a liquid heating bag and a bag heating means, in particular, for heating cooled blood to a temperature suitable for a transfusion. Such a liquid heating bag comprises a flow volume formed from at least two flexible plastic foils which are preferably connected to each other at four delimiting edges, wherein the flow volume has a flat, substantially trapezoidal basic shape which is delimited by the delimiting edges. An inlet line opening and an outlet line opening are provided on the flow volume for a liquid to be heated.

A blood heating system which consists of a blood heating bag and a bag heating means is used for heating natural blood for transfusion purposes or for dialysis as well as for transfusion of blood plasma or other liquids.

Blood is usually kept at a temperature of approximately 4° C. Prior to use, the blood must be heated to body temperature of approximately 37° C. The blood which is used for transfusions must not have an excessively low or an excessively high temperature. In particular, in case of an emergency, the blood must be heated very quickly, since it is not possible to keep heated blood ready for possible emergencies. In case of an emergency, the blood must be heated quickly and also the handling of the blood heating system must be simple and rapid. The stated temperature conditions must be maintained irrespective of the flow rate of the blood through the blood heating system. This flow rate may be over 5 liters per hour for infusions under pressure. To avoid overheating, the temperature of the bag heating means may only be slightly above the body temperature with the consequence that the bag heating means must provide a large heat exchanging surface to obtain sufficient thermal transfer.

Prior art discloses bag heating means of various designs. A distinction can be drawn between bag heating means for inserting a liquid heating bag, having a chamber that can be opened and that is closed during heating of the inserted liquid heating bag, and into which the liquid heating bag is inserted, and bag heating means for inserting a liquid heating bag into a gap formed between two heat exchanger plates that are fixed parallel to each other using fastening means. The bag heating means having a chamber which can be opened are relatively difficult to handle and are therefore of limited use in emergencies.

When a liquid, for example, blood, is heated by means of a blood heating system, gases dissolved in the blood can be released, resulting in the formation of gas bubbles in the liquid heating bag. These gas bubbles must not enter the body of the patient receiving the blood, since they could produce an embolism. Precautions must therefore be taken to avoid the entry of gas bubbles. This can be done, for example, by visual monitoring of the blood transfusion. U.S. Pat. No. 6,572,641 discloses a liquid heating bag of the inventive kind that, in addition to the inlet line opening and the outlet line opening, has a degassing opening terminating in a gas reception volume that is part of the flow volume. This degassing opening is disposed in the region of an upper limiting edge that is to be disposed at the top during liquid heating and is located above the outlet line opening. In this way, upwardly rising gas bubbles are captured in the gas reception volume and are removed through the degassing opening. In this liquid heating bag, the degassing opening extends relatively far into the gas reception volume, so that the liquid level of the liquid to be heated is above the degassing opening. This can result in loss of liquid. For this reason, one free end of a tube connected to the degassing opening has liquid flow prevention means providing a seal against the passage of liquid. In this liquid heating bag, the inlet line opening, the outlet line opening, and the degassing opening are each disposed at different delimiting edges, i.e. sides of the liquid heating bag. This makes handling the liquid heating bag more difficult because tubes connected to the openings lead out of the bag heating means used for heating.

A blood heating system with a more easily handled liquid heating bag of the inventive kind is described in DE 10 2004 026 446 A1. In this liquid heating bag, the inlet line opening and the outlet line opening are disposed on an upper delimiting edge to be disposed at the top during liquid heating. The upper delimiting edge extends sufficiently obliquely with respect to its adjacent delimiting edges that an acute angle is subtended between the upper delimiting edge and a delimiting edge adjacent thereto. This acute angle includes an upper flow volume region into which the outlet line opening opens. Furthermore, a liquid flow guiding seam is provided that is formed by connecting the plastic foils in the region of the flow volume and that divides the upper delimiting edge into a lower inlet line opening region and an upper outlet line opening region. At the openings of this liquid heating bag, the inlet and outlet lines protrude in an ordered fashion upward out of the bag heating means used. However, this liquid heating bag has no degassing opening.

The object of the invention is to provide a liquid heating bag and a bag heating means that avoid the disadvantages of prior art. In particular, the bag should reliably avoid gas bubbles entering the outlet line opening while avoiding loss of the liquid to be heated.

SUMMARY OF THE INVENTION

This object is achieved by the liquid heating bag and bag heating means of the independent claims. The dependent claims articulate preferred embodiments of the invention.

The inventive liquid heating bag comprises a flow volume formed from at least two flexible plastic foils which are preferably connected to each other at four delimiting edges. The flow volume has a flat, substantially trapezoidal basic shape which is delimited by the delimiting edges. An inlet line opening and an outlet line opening are provided on the flow volume for a liquid to be heated that are disposed on an upper delimiting edge that is to be disposed upwardly during liquid heating. The upper delimiting edge extends sufficiently obliquely with respect to its adjacent delimiting edges that a gas reception volume is formed in an acute angle of the flow volume subtended between the upper delimiting edge and a delimiting edge adjacent thereto. The upper delimiting edge is divided into a lower inlet line opening region and an upper outlet line opening region on the gas reception volume side by a liquid flow guiding seam that is formed by connecting the plastic foils in the region of the flow volume. According to the invention, a degassing opening is disposed at the upper delimiting edge in the region of the gas reception volume between the outlet line opening and the delimiting edge adjacent to the outlet line opening region. The degassing opening is therefore located higher than the outlet line opening in the disposition during use.

The inventive liquid heating bag combines the advantages of the blood bags disclosed in DE 10 2004 026 446 A1 and U.S. Pat. No. 6,572,641. Because the degassing opening is disposed in the region of the acute angle of the basic shape of the blood bag, the liquid level of the liquid to be heated in the gas reception volume is in a relatively narrow volume region, so that a volume of gas that is sufficient to avoid loss of liquid and easy to monitor already arises from a slight occurrence of gas bubbles. The liquid level can therefore be easily controlled so that the degassing opening is always above the liquid level. The openings of the inventive liquid heating bag are all disposed at the upper delimiting edge so that tubes connected thereto can easily be guided in an ordered fashion. This is important to avoid complications, for example, due to disconnected tubes, in particular, during emergency situations in which the attention of helpers is focused on the patients.

A separating seam departing from the upper delimiting edge and protruding into the flow volume is preferably provided between the outlet line opening and the degassing opening, which partially separates the gas reception volume from the flow volume. This guides the flow of the liquid to be heated in the liquid heating bag along a defined path so that even heating is ensured.

A gas bubble guiding edge is very advantageously formed at the liquid flow guiding seam that, departing from the liquid flow guiding seam, projects into the volume of the flow volume on the outlet line opening side to a sufficient extent that the free end of the separating seam is spaced from the liquid flow guiding seam. This redirects gas bubbles that arise in the region below the outlet line opening to the degassing opening side of the separating seam and therefore into the gas reception volume. This particularly reliably avoids gas bubbles being guided out through the outlet line opening.

If at least one gas bubble rise impediment edge that forms a gas collection volume is provided in the outlet line opening side volume of the flow volume, accumulation of gas bubbles, that is, foam extending into the region of the outlet line opening can be made additionally difficult. In addition, a material promoting the separation of the gas from the liquid can be inserted if necessary into the gas collection volume (porous body and/or foam, etc.) to ensure safe separation of gas and liquid.

For especially simple introduction of the inventive liquid heating bag into a bag heating means, it is advantageous to dispose an insertion tab on one of the lower delimiting edges opposite the upper delimiting edge. The insertion tab can be formed as a part of the plastic foils that projects past the lower delimiting edge. This tab can comprise openings and/or rings that ensure fastening of the bag in the correct position. In a further embodiment, while the bag is inserted in the bag heating means, the gap with the liquid inlet and outlet lines and the gas outlet line can be covered so that no liquid can enter this gap. This cover can be part of the bag and/or bag heating means.

Inventive liquid heating bags that can be produced at low cost and used as disposable bags can be manufactured by forming the flow volume by welding the plastic foils directly to each other at the delimiting edges and forming the liquid flow guiding seam as a welding seam between the plastic foils.

If the basic shape of the inventive liquid heating bag is elongated, the flow resistance through the liquid heating bag is kept low and the residual liquid can be easily squeezed out of the liquid heating bag. The upper and lower delimiting edges located opposite each other are constituted as narrow edges and the delimiting edges connecting the upper and the lower delimiting edges essentially extend parallel to each other and are constituted as long sides. The liquid flow guiding seam extends essentially parallel to the long sides, starting at the upper delimiting edge.

An inventive bag heating means is suitable for introducing a liquid heating bag and has heating elements that form two substantially rectangular heat exchanger plates each having a substantially flat heat exchanging surface. The heat exchanger plates are disposed opposite each other with their heat exchanging surfaces having a mutual distance from each other such that a gap is formed between the heat exchanging surfaces, with a gap width suitable for receiving the liquid heating bag. According to the invention, at least one liquid sensor and/or one monitoring opening for detection of a liquid level is provided in the region of the heat exchanger surfaces in the liquid heating bag inserted in the bag heating means. In this way, the liquid level in the inserted liquid heating bag can be easily observed to ensure avoidance of gas bubbles flowing out into the outlet line opening and to ensure that no liquid flows out through the degassing opening.

If the bag heating means has three grooved shoulders at an upper narrow side edge of the heat exchanger plates, it is especially suitable for use with an inventive liquid heating bag. The grooved shoulders are shaped complementarily to the inlet line opening and the outlet line opening and the degassing opening of a liquid heating bag inserted into the bag heating means such that an inlet line connected to the liquid heating bag and an outlet line connected to the liquid heating bag and a degassing line connected to the liquid heating bag are positively held in the grooved shoulders while the liquid heating bag is inserted into the bag heating means.

A cavity, in particular, a cut recess, for shaping the gas reception volume of the liquid heating bag is preferably formed in at least one of the heat exchanger plates in the region adjacent to the upper narrow side edge of the heat exchanger plate.

A degassing valve for connecting the degassing opening of the liquid heating bag introduced into the bag heating means, preferably through a tube is especially preferably provided. By opening or closing the degassing valve, it is possible to control the liquid level in the liquid heating bag inserted into the bag heating means.

The liquid level sensor and the degassing valve are very advantageously connected to a control unit of the bag heating means. The control unit is set up in such a way as to control the degassing valve to close the degassing opening when the liquid level detected by the liquid level sensor rises above a predefined liquid level in the gas reception volume of the liquid heating bag and to control the degassing valve to open the degassing opening and/or to control pumping away of the gas in the gas reception volume by means of a pump when the liquid level detected by the liquid level sensor falls below the predefined liquid level in the gas reception volume of the liquid heating bag. In this way, monitoring and closed-loop control of the liquid level in the liquid heating bag, that is, in the gas reception volume of the liquid heating bag, can be performed automatically.

In an inventive bag heating means, the heat exchanger plates can be mounted to each other on a first long side edge of the heat exchanger plates via fastening means such that the heat exchanging surfaces are fixed substantially parallel to each other via the fastening means, wherein the gap is open along a second long side edge and the narrow side edges of the heat exchanger plates. This makes insertion of an inventive liquid heating bag into the bag heating means very fast and simple. The fastening means can be resilient such that a pressure change in the liquid heating bag, which is inserted into the bag heating means changes the gap width, wherein a pressure increase widens the gap and pressure reduction reduces the size of the gap. This variation in the gap width already automatically results in regulation of the liquid level in the liquid heating bag because the pressure in the liquid heating bag is largely kept constant.

Devices, for example, a tube heating or drip chamber, which are commonly used for infusions or transfusions, may be disposed on the outlet line extending to the patient.

An inventive liquid heating system comprises an inventive bag heating means and, in particular, an inventive liquid heating bag.

The invention is explained in more detail below using embodiments and with reference to the drawings.

BRIEF DESCRIPTION OF THE DRAWING

FIG. 2b shows a schematic cross-section through the bag heating means with an inserted liquid heating bag.

DESCRIPTION OF THE PREFERRED EMBODIMENT

The figures of the drawings show the inventive object in a highly schematized manner and are not to be taken to scale. The individual components of the inventive object are illustrated such that their construction is clearly shown.

Figure 1A:
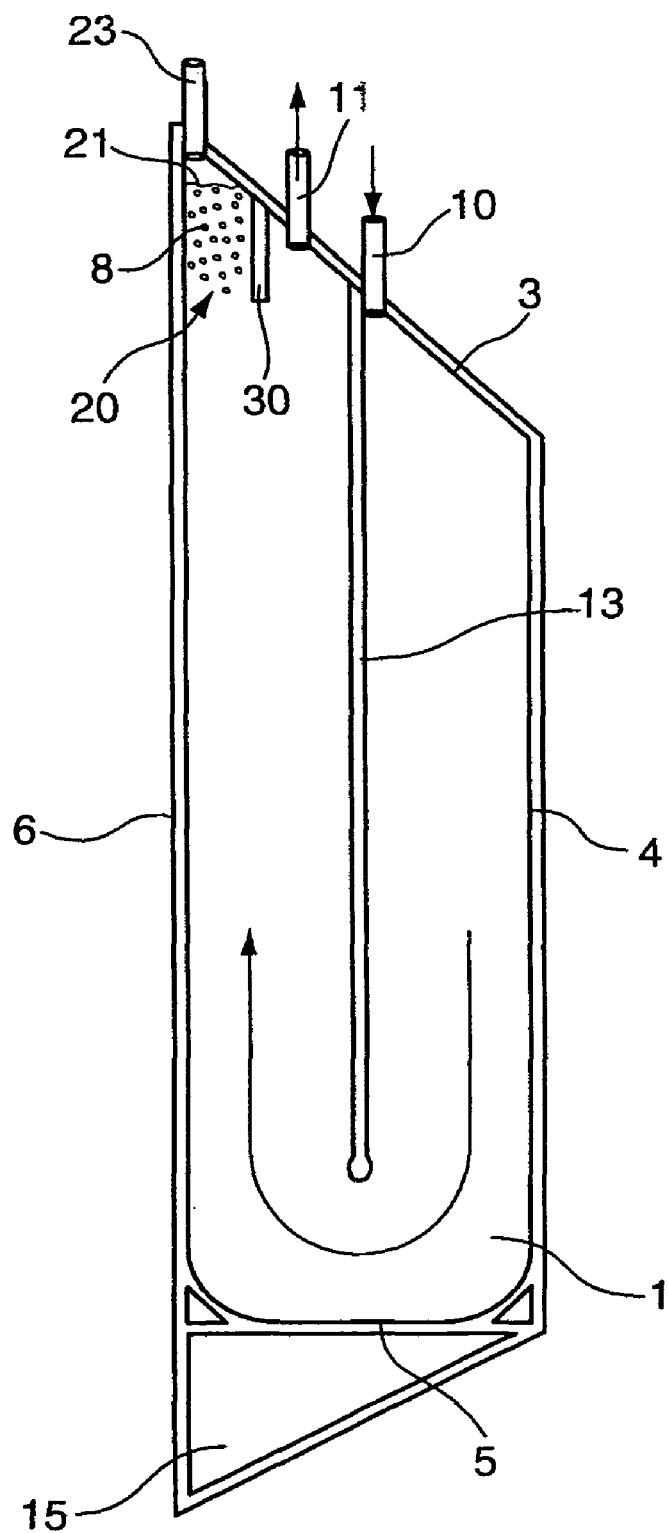
FIGS. 1a to 1c show different embodiments of an inventive liquid heating bag.
Figure 1B:
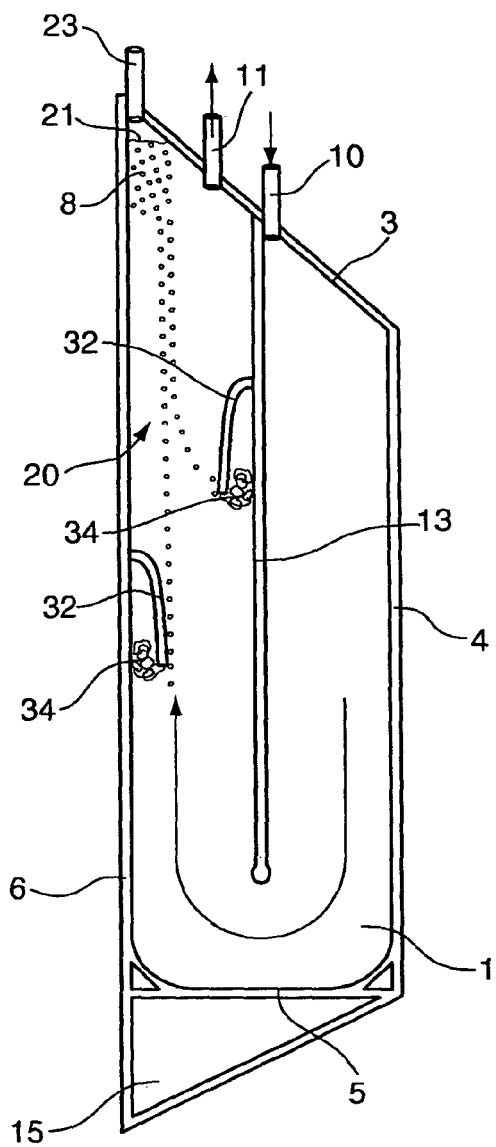
Figure 1C:
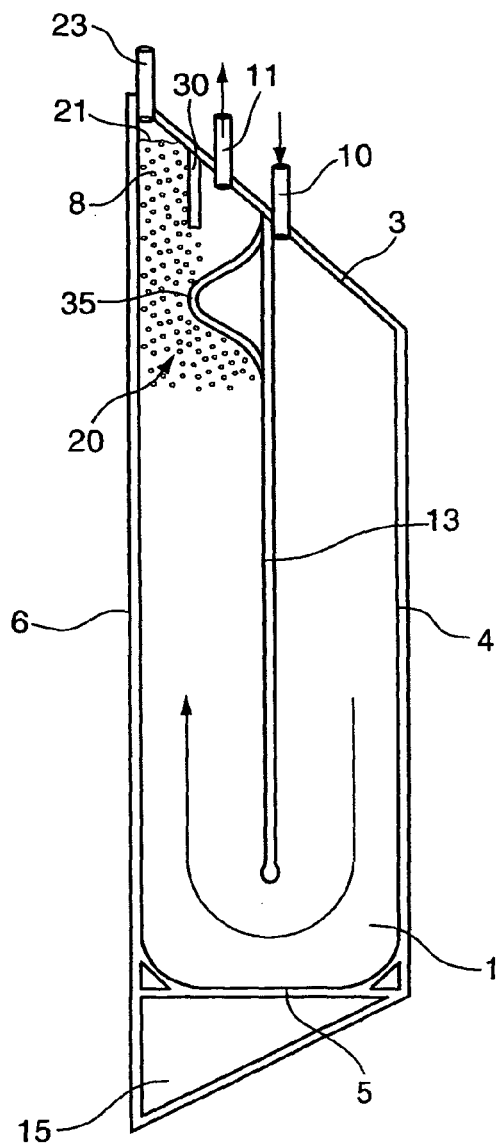

FIGS. 1a to 1c show various embodiments of an inventive liquid heating bag. The liquid heating bags each have a flow volume 1 that is formed from two flexible plastic foils connected to each other, for example, by welding at four delimiting edges 3,4,5,6. The flow volume 1 has a flat, substantially trapezoidal basic shape that is limited by the delimiting edges 3,4,5,6. The upper delimiting edge 3 to be disposed at the top during liquid heating extends sufficiently obliquely with respect to its adjacent delimiting edges 4,6 that a gas reception volume 8 is formed in an acute angle of the flow volume 1 subtended between the upper delimiting edge 3 and a delimiting edge 6 adjacent thereto.

At the upper delimiting edge 3, one inlet line opening 10 and one outlet line opening 11 are each disposed for the liquid to be heated. In the figures, the direction of flow of the liquid is symbolically shown with arrows. The upper delimiting edge 3 is divided by a liquid flow guiding seam 13 that is formed by connecting the plastic foils in the region of the flow volume 1 into a lower inlet line opening region and an upper outlet line opening region on the gas reception volume side. This ensures that the liquid, during heating, always takes the same flow path through the liquid heating bag and is heated evenly.

The basic shape of the liquid heating bag shown is elongated, wherein the upper delimiting edge 3 and the lower delimiting edge 5 located opposite each other are constituted as narrow edges and the delimiting edges 4,6 connecting the upper and the lower delimiting edges essentially extend parallel to each other and are constituted as long sides. The liquid flow guiding seam 13 extends, starting at the upper delimiting edge 3, essentially parallel to the long sides. An insertion tab 15 is formed at the lower delimiting edge 5 opposite the upper delimiting edge 3. This insertion tab 15 is formed as part of the plastic foils that projects past the lower delimiting edge 5.

Gas bubbles 20 arising during heating collect in the gas reception volume 8. Liquid to be heated in the liquid heating bag therefore forms a liquid level 21, that is, a liquid surface, in the gas reception volume 8. A degassing opening 23 is disposed on the upper delimiting edge 3 in the region of the gas reception volume 8 between the outlet line opening 11 and the delimiting edge 6 adjacent to the outlet line opening region, through which the gas of the gas bubbles 20 can be removed from the liquid heating bag. The degassing opening 23 is therefore further toward the top than the outlet line opening 11 for the heated liquid, preferably in the top corner of the gas reception volume 8, so that rising gas bubbles 20, and therefore any foam that may have formed, accumulate above the outlet line opening 11.

In the embodiments of the inventive liquid heating bag shown in FIGS. 1a and 1c, in each case, a separating seam 30 is provided between the outlet line opening 11 and the degassing opening 23 departing from the upper delimiting edge 3 and protruding into the flow volume 1 that partially separates the gas reception volume 8 from the flow volume 1. The separating seam 30 can be constituted, for example, as a weld seam of the plastic foils constituting the liquid heating bag.

In the embodiment of the inventive liquid heating bag shown in FIG. 1b, two gas bubble rise impediment edges 32 are provided in the outlet line opening side volume of the flow volume 1 that each form a gas collection volume. The gas bubble rise impediment edges 32 form an open volume delimitation in the downward direction, that is, toward the lower delimiting edge 5. They protrude sufficiently far into the flow volume 1 that overflowing gas bubbles 20 that originate, for example, from the foam 34 accumulating in the gas collection volumes are guided to the gas reception volume 8 via the free end of the gas bubble rise impediment edges 32. The gas bubble rise impediment edges 32 can also be constituted, for example, as weld seams of the plastic foils forming the liquid heating bag.

In the embodiment of the inventive liquid heating bag shown in FIG. 1c, in addition to the separating seam 30 in the outlet line opening side volume of the flow volume, a gas bubble guiding edge 35 is formed on the liquid flow guiding seam 13. Departing from the liquid flow guiding seam 13, the gas bubble guiding edge 35 protrudes into the outlet opening side volume of the flow volume 1 at least as far as the free end of the separating seam 30 is separated from the liquid flow guiding seam 13. The gas bubble guiding edge 13 can also be constituted, for example, as a weld seam of the plastic foils forming the liquid heating bag. Gas bubbles from the liquid to be heated are thus guided away from the outlet line opening 11 to collect in the gas reception volume 8.

Figure 2A:
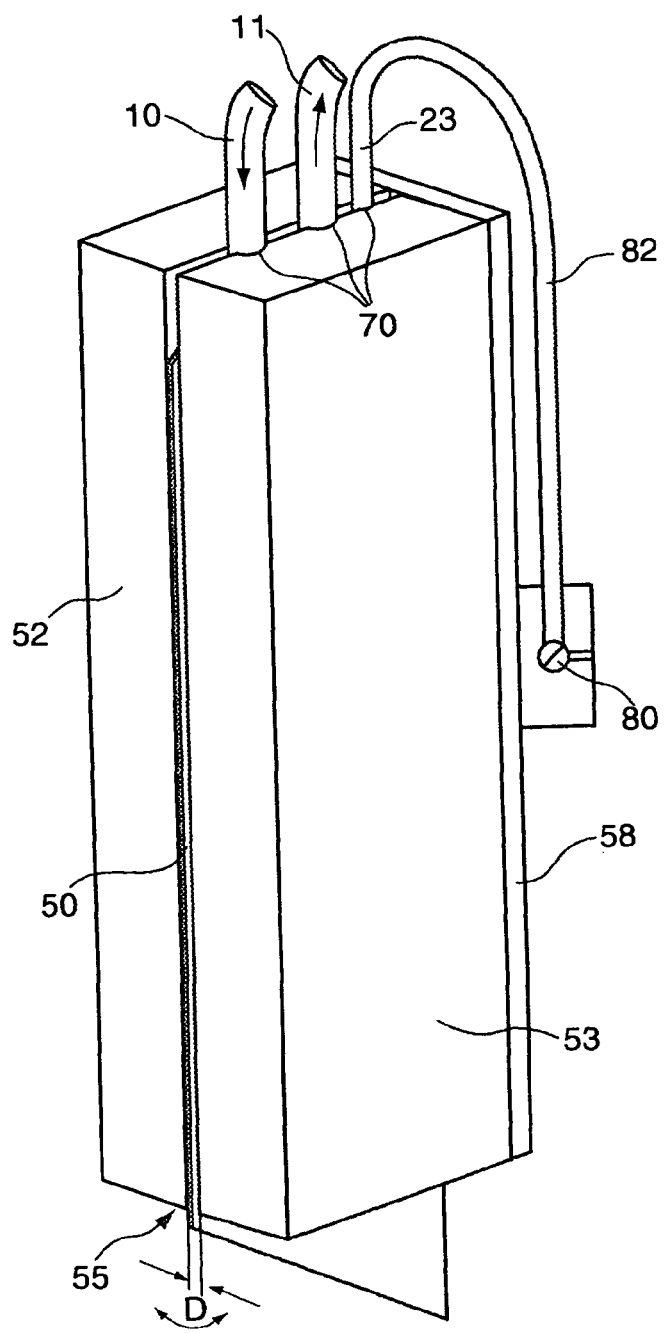
FIGS. 2a and 2b show an inventive bag heating means with an inventive liquid heating bag inserted.
Figure 2B:
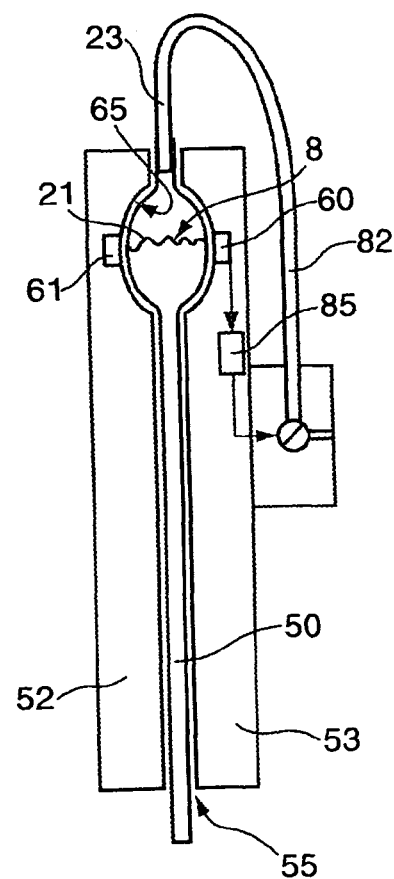

FIGS. 2a and 2b show an inventive bag heating means with an inventive liquid heating bag 50 inserted, wherein FIG. 2b shows a schematic cross-section through the bag heating means with a liquid heating bag 50 inserted. To heat the liquid to be heated in liquid heating bag 50, the bag heating means comprises two essentially rectangular heat exchanger plates 52,53 as heating elements. The heat exchanger plates 52,53 each constitute a heat exchange surface inside the bag heating means. The heat exchanger plates 52,53 are disposed opposite each other with their heat exchanging surfaces having a distance from each other such that a gap 55 is formed between the heat exchanging surfaces, with a gap width D suitable for receiving the liquid heating bag 50.

The heat exchanger plates 52,53 are mounted to each other on a first long side edge of the heat exchanger plates 52,53 via fastening means 58 such that the heat exchanging surfaces are fixed substantially parallel to each other via the fastening means 58. The gap 55 is open along a second long side edge and the narrow side edges of the heat exchanger plates, which simplifies insertion of the liquid heating bag 50 between the heat exchanger plates 52,53. The fastening means 58 are resilient such that a pressure change in the liquid heating bag 50, which is inserted into the bag heating means, changes the gap width D, wherein a pressure increase widens the gap and pressure reduction reduces the size of the gap 55, as is symbolically shown in FIG. 2a by a curved double arrow.

A liquid sensor 60 is provided in the region of the heat exchanger surfaces for detecting a liquid level 21 in the liquid heating bag 50 inserted into the bag heating means. The liquid sensor 60 can, for example, be constituted as a light detector in the heat exchange surface of one of the heat exchanger plates 52,53, wherein a light source 61, for example, a light-emitting diode can be disposed in the region of the heat exchange surface of the other heat exchanger plate 52 opposite the liquid level sensor 60. Light emitted by the light source 61 is detected by the liquid level sensor 60 more or less attenuated depending on the liquid level. In the region of the heat exchanger plates 52,53 adjacent to the upper narrow side edge of the heat exchanger plate 52,53, a cavity 65 is formed to shape the gas reception volume 8 of the liquid heating bag 50. The liquid heating bag 50 is therefore located between the heat exchanger plates 52,53 such that the gas reception volume 8 of the liquid heating bag 50 is positioned in the region of the cavity 65. The liquid level sensor 60 is also positioned in the region of this cavity 65 so that the liquid level 21 can be detected in the liquid heating bag 50 in the region of the gas reception volume 8.

The liquid sensor 60 can also have a different design and can, for example, be supplemented or replaced by an ultrasound sensor or by a different gas bubble detection technology.

The bag heating means has three grooved shoulders 70 at the upper narrow side edge of the heat exchanger plates 52,53 that are shaped complementarily to the inlet line opening 10, the outlet line opening 11, and the degassing opening 23 of the liquid heating bag 50 inserted into the bag heating means such that an inlet line connected to the liquid heating bag 50 and an outlet line connected to the liquid heating bag 50 as well as a degassing line connected to the liquid heating bag 50 are positively held in the grooved shoulders 70 while the liquid heating bag 50 is inserted into the bag heating means. Degassing valve 80 is provided on the bag heating means for connecting the degassing opening 23 of the liquid heating bag 50 inserted into the bag heating means via a tube 82. The degassing opening 23 can thereby be variably opened and closed by means of the degassing valve 80. The liquid level sensor 60 and the degassing valve 80 are connected to a control unit 85. The control unit 85 is set up in such a way as to control the degassing valve 80 to close the degassing opening 23 when the liquid level 21 detected by the liquid level sensor 60 rises above a predefined liquid level in the gas reception volume 8 of the liquid heating bag 50 and to control the degassing valve 80 to open the degassing opening 23 when the liquid level 21 detected by the liquid level sensor 60 falls below the predefined liquid level in the gas reception volume 8 of the liquid heating bag 50. The associated signal flow is symbolized in FIG. 2b by the arrowheads of the connections between the liquid level sensor 60 and control unit 85 and between the control unit 85 and degassing valve 80.

A liquid heating bag 50 is proposed, in particular, a blood heating bag, with a flow volume 1 that is formed from at least two flexible plastic foils connected to each other by welding at four delimiting edges 3,4, 5, 6, having a flat, substantially trapezoidal basic shape that is limited by the delimiting edges 3,4,5,6, and an inlet line opening 10 and an outlet line opening 11 for a liquid to be heated that are disposed at an upper delimiting edge 3 of the delimiting edges 3,4,5,6 to be disposed at the top during liquid heating, wherein the upper delimiting edge 3 extends sufficiently obliquely with respect to its adjacent delimiting edges 4,6 that a gas reception volume 8 is formed in a region of an acute angle of the flow volume 1 subtended between the upper delimiting edge 3 and a delimiting edge 6 adjacent thereto, and a liquid flow guiding seam 13 that is formed by connecting the plastic foils in the region of the flow volume 1 and divides the upper delimiting edge 3 into a lower inlet line opening region and an upper outlet line opening region on the gas reception volume side. A degassing opening 23 is disposed at the upper delimiting edge 3 in the region of the gas reception volume 8 between the outlet line opening 11 and the delimiting edge 6 adjacent to the outlet line opening region.

The invention is not limited to the above-mentioned embodiments. A plurality of variants is feasible which utilize the features of the invention even if they have a different basic design.

We claim:

1. A liquid heating bag or a blood heating bag, the bag defining a flow volume for a liquid being heated, the bag comprising:
   a first flexible plastic foil;
   at least one second flexible plastic foil connected to said first foil to form a flat, substantially trapezoidal basic shape defined by delimiting edges, said delimiting edges including an upper delimiting edge disposed at a top of the bag during liquid heating and an adjacent delimiting edge, wherein said upper delimiting edge extends obliquely with respect to said adjacent delimiting edge to define a gas reception volume in an acute angular region subtended between said upper delimiting edge and said adjacent delimiting edge;
   a liquid inlet line opening disposed at said upper delimiting edge;
   a liquid outlet line opening disposed at said upper delimiting edge at a separation from said inlet line opening;
   a liquid flow guiding seam disposed between said inlet and said outlet openings, said guiding seam formed by connecting said first and said second plastic foils in a region of the flow volume, thereby dividing said upper delimiting edge into a lower inlet line opening region and an upper outlet line opening region disposed at a gas reception volume side of the bag; and
   a degassing opening disposed at said outlet line opening region of said upper delimiting edge proximate to said gas reception volume and between said outlet line opening and said adjacent delimiting edge.

2. The liquid heating bag of claim 1, further comprising a separating seam disposed between said outlet line opening and said degassing opening and extending from said upper delimiting edge to protrude into the flow volume and partially separate said gas reception volume from the flow volume.

3. The liquid heating bag of claim 2, further comprising a gas bubble guiding edge formed at said liquid flow guiding seam and extending from said liquid flow guiding seam to protrude into an outlet opening sided volume of the flow volume, at least as far as a free end of said separating seam is separated from said liquid flow guiding seam.

4. The liquid heating bag of claim 1, further comprising at least one gas bubble rise impediment edge disposed in an outlet line opening sided volume of the flow volume to form a gas collection volume.

5. The liquid heating bag of claim 1, further comprising an insertion tab disposed on a lower delimiting edge opposite said upper delimiting edge, said insertion tab being formed as a part of plastic foil that projects past said lower delimiting edge.

6. The liquid heating bag of claim 1, wherein the flow volume is defined by welding said first and said second plastic foils directly to each other at said delimiting edges, said liquid flow guiding seam being constituted as a weld seam between said first and said second plastic foils.

7. The liquid heating bag of claim 1, wherein said basic shape is elongated and said upper delimiting edge is opposite to a lower delimiting edge, said upper and lower delimiting edges being narrow edges, wherein delimiting edges connected between said upper and said lower delimiting edges essentially extend parallel to each other to form long sides, said liquid flow guiding seam extending from said upper delimiting edge substantially parallel to said long sides.

8. A bag heating means for the liquid heating bag of claim 1, the bag heating means comprising:
- a first substantially rectangular heat exchanger plate constituting a heating element and having a first flat heat exchanging surface;
- a second substantially rectangular heat exchanger plate constituting a heating element and having a second flat heat exchanging surface, said first and said second heat exchanger plates being disposed opposite each other such that said first and said second heat exchanging surfaces define a gap, said gap having a width suitable for receiving the liquid heating bag;
- at least one liquid level sensor and/or means defining a monitoring opening for detection of a liquid level in the liquid heating bag; and
- means defining three grooved shoulders disposed at an upper narrow side edge of said first and said second heat exchanger plates, said grooved shoulders being shaped complementarily to said inlet line opening, said outlet line opening, and said degassing opening, wherein an inlet line connected to said liquid inlet line opening, an outlet line connected to said liquid outlet line opening, and a degassing line connected to said degassing opening are positively held in said grooved shoulders while the liquid heating bag is inserted into the bag heating means.

9. The bag heating means of claim 8, wherein at least one of said first and said second heat exchanger plates has a cavity or a cut recess in a region adjacent to said upper narrow side edge of said first and said second heat exchanger plates for shaping said gas reception volume of the liquid heating bag.

10. The bag heating means of claim 8, further comprising a degassing valve means for connecting said degassing opening of the liquid heating bag when the bag is inserted into the bag heating means.

11. The bag heating means of claim 10, wherein said degassing valve means comprises a tube.

12. The bag heating means of claim 10, wherein said liquid level sensor and said degassing valve means are connected to a control unit, the control unit being structured to control said degassing valve means for closing said degassing opening when a liquid level detected by said liquid level sensor rises above a predefined liquid level in said gas reception volume of the liquid heating bag and to control said degassing valve means to open said degassing opening and/or to control pumping away of gas in said gas reception volume when the liquid level detected by said liquid level sensor falls below the predefined liquid level in said gas reception volume of the liquid heating bag.

13. A liquid heating system having the bag heating means of claim 8.

* * * * *